United States Patent [19]
Sowerby et al.

[11] Patent Number: 5,831,150
[45] Date of Patent: Nov. 3, 1998

[54] DETERMINING THE SIZE DISTRIBUTION OF PARTICLES IN A FLUID

[75] Inventors: Brian David Sowerby, Kareela; Peter John Coghill, Punchbowl, both of Australia

[73] Assignee: Commonwealth Scientific and Industrial Research Organisation, Australia

[21] Appl. No.: 981,157
[22] Filed: Mar. 26, 1998

[30] Foreign Application Priority Data

Jun. 19, 1995 [AU] Australia ................................. PN3637
Jul. 18, 1995 [AU] Australia ................................. PN4233

[51] Int. Cl.⁶ .................................................. G01N 15/02
[52] U.S. Cl. .......................................................... 73/61.75
[58] Field of Search ................................ 73/28.01, 597, 73/865.5, 602, 61.75

[56] References Cited

U.S. PATENT DOCUMENTS

| 3,529,153 | 9/1970 | Zimmerman et al. | 250/43.5 |
| 4,283,953 | 8/1981 | Plona | 73/589 |
| 5,121,629 | 6/1992 | Alba | 73/61.41 |

FOREIGN PATENT DOCUMENTS 0 044 596  1/1982  European Pat. Off. .
1 485 750  9/1977  United Kingdom .

OTHER PUBLICATIONS

Patent Abstracts of Japan, C–1195, page 8, JP–6–22956 A (Yokogawa Medical Syst) 1 Feb. 1994.
Patent Abstracts of Japan, P–413, page 106, JP 60–147607 A (Hitachi Seisakusho) 3 Aug. 1985.

*Primary Examiner*—Robert Raevis
*Attorney, Agent, or Firm*—Kenyon & Kenyon

[57] ABSTRACT

In this embodiment the size distribution of particles in a fluid is determined by performing the following steps: (a) passing a plurality of ultrasonic beams through the fluid, wherein the beams have respective frequencies; (b) obtaining a velocity measure of the beams in the fluid; (c) obtaining an ultrasonic velocity spectrum as a function of particle size for the fluid; (d) determining from the attenuation of gamma-rays the density of the fluid; and (3) calculating the particle size distribution for the fluid from the velocity measure, the velocity spectrum, and the suspension density which were respectively obtained in steps (b), (c) and (d).

17 Claims, 4 Drawing Sheets

DETERMINING THE SIZE DISTRIBUTION OF PARTICLES IN A FLUID

The present invention relates to a method and apparatus for determining the size distribution of particles in a fluid.

The term fluid is intended to include both a liquid and the solid particles contained in that liquid. Examples include slurries and other suspensions.

The invention has been developed primarily for use with opaque slurries in the mineral and paint industries and will be described hereinafter with reference to that application. However, the invention is not limited to these particular fields of use and can also be used to determine size distribution of particles in other suspensions and in other industries such as the chemical, pigment, pharmaceutical, food and cosmetic industries, amongst others. The invention is particularly applicable to on-line particle size analysis for the control of grinding, crystallisation, precipitation and agglomeration processes.

It is preferable to use on-line particle size analysers to negate the need for side stream or dilution of the fluid being analysed. Hitherto, such analysers have made use of either the attenuation experienced by one or more ultrasonic beams directed through the fluid, laser scanning or laser diffraction.

It is an object of the present invention, at least in the preferred embodiment, to provide a method and apparatus for determining the size distribution of particles in a fluid using a velocity measure of a plurality of ultrasonic beams at different frequencies in said fluid.

According to one aspect of the invention there is provided a method for determining the size distribution of particles in a fluid, the method including the steps of:

(a) passing a plurality of ultrasonic beams through the fluid, wherein the beams have respective frequencies $f_1$, $f_2$, ... $f_n$;

(b) obtaining a velocity measure of the beams in the fluid;

(c) obtaining an ultrasonic velocity spectrum as a function of particle size for the fluid; and (d) calculating the particle size distribution for the particles in the fluid from the velocity measure and the velocity spectrum which were respectively obtained in steps (b) and (c).

Preferably, the ultrasonic velocity spectrum is obtained either by prior experiment or calculation.

Preferably, step (c) includes transforming the velocity spectrum into a linear form. More preferably, step (d) includes an inversion of the linear form.

Preferably also, the method includes the steps of:

(e) passing gamma rays through the fluid;

(f) determining from the attenuation of the gamma-rays the density of the fluid; and (g) calculating the particle size distribution of the particles in the fluid from the velocity measure, the velocity spectrum, and the density measure respectively obtained during steps (b), (c) and (f).

Preferably step (g) includes an inversion of the linear form to give the particle size distribution in a certain size range. In an alternate embodiment, the amount of particles outside the inversion size range is also calculated.

Preferably also, step (b) includes determining the difference in velocity of the beams having frequencies $f_i$ and $f_{i+1}$. In alternative embodiments, however, step (b) includes determining the velocity of each of the beams.

According to another aspect of the invention there is provided an apparatus for determining the size distribution of particles in a fluid, the apparatus including:

transducer means for passing a plurality of ultrasonic beams through the fluid, wherein the beams have respective frequencies $f_1$, $f_2$ ... $f_n$;

first processor means for obtaining a velocity measure of said beams in the fluid;

second processor means for obtaining the ultrasonic velocity spectrum as a function of particle size for the fluid; and third processor means responsive to the first and second processor means for calculating the particle size distribution for the fluid.

Preferably, the first, second and third processors are incorporated in a single processor.

A preferred embodiment of the invention will now be described, by way of example only, with reference to the accompanying drawings in which.

Figure 1:
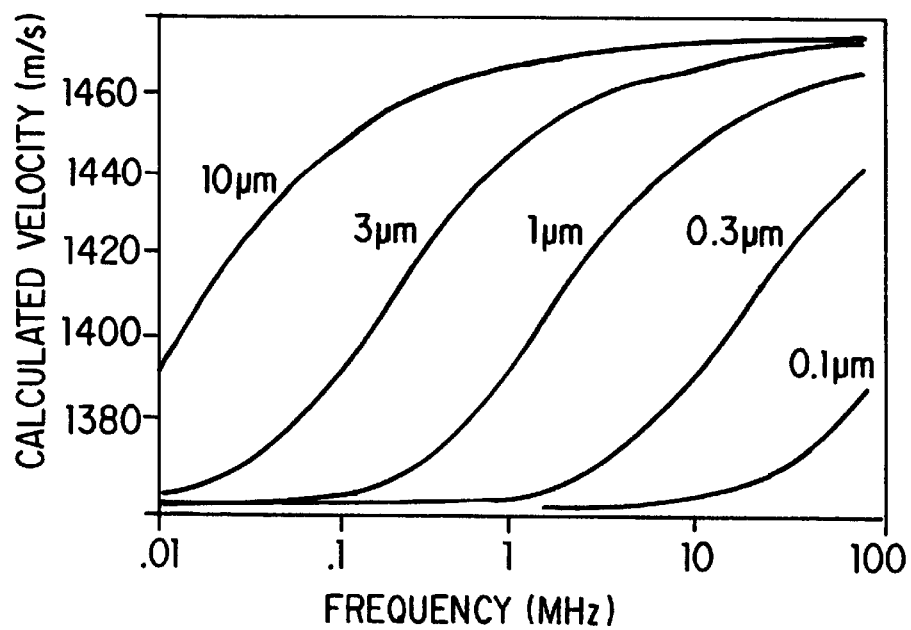
FIG. 1 is a graph illustrating the variation of velocity of an ultrasonic beam through a fluid containing particles of various sizes as calculated using a theoretical model.

In this embodiment the size distribution of particles in a fluid is determined by performing the following steps:

(a) passing a plurality of ultrasonic beams through the fluid, wherein the beams have respective frequencies $f_1$, $f_2$, ... $f_n$;

(b) obtaining a velocity measure of the beams in the fluid;

(c) obtaining an ultrasonic velocity spectrum as a function of particle size for the fluid;

(d) determining from the attenuation of gamma-rays the density of the fluid; and (e) calculating the particle size distribution for the fluid from the velocity measure, the velocity spectrum, and the suspension density which were respectively obtained in steps (b), (c) and (d).

In this embodiment the velocity measure is the differences between velocities at different frequencies. This is particularly advantageous because the changes in velocity are small compared to the total velocity. Moreover, compared to total velocity measurements, velocity differences are less sensitive to temperature changes and air bubbles in the fluid.

For the fluids under consideration, the difference in velocity is best expressed by the matrix equation:

$$D = RM \qquad (1)$$

where $D = \{d_i, \ldots d_m\}$ whose elements $d_m$ represent the measured velocity differences between each pair of frequencies $f_i$ and $f_{i+1}$. Additionally, $R = \{r_1, \ldots r_n\}$ whose elements $r_n$ represent the volume fraction of particles in the fluid in each successive size range, while M is a matrix of calculated velocity differences whose elements are given by:

$$mij = V(f_{j+1}, a_{i,\rho}) - V(f_j, a_{i,\rho}) \qquad (2)$$

In equation 2, V is the velocity calculated in step (b) above, $\rho$ is the total volume fraction of solids as measured by a gamma-ray attenuation gauge, and $a_i$ is the radius of the $i^{th}$ size bin. In addition, there is the important constraint that:

$$\rho = \sum_{i=1}^{n} r_1 \qquad (3)$$

During step (d) the matrix equation is inverted to determine the values of $r_1 \ldots r_n$. As with most indirect methods of measurement, the results of direct inversion:

$$R = DM^{-1} \qquad (4)$$

can be unstable and sensitive to small measurement errors. However, satisfactory results are obtained with the use of inversion algorithms such as that described by Twomey, S. in "Introduction to the mathematics of inversion in remote sensing and indirect measurements", Developments in Geomathematics 3, Elsevier Amsterdam 1977, the contents of which are incorporated herein by way of cross reference. Twomey describes various techniques for inverting such equations without introducing unwanted oscillations into the solution. An iteration technique due to Chahine and described in Twomey was chosen for the present work, although alternative techniques are available. Iteration is carried out until the RMS error between the experimental and calculated results is similar to the measurement error. The adopted technique has the advantages of automatically ensuring that all elements of R are positive and allowing normalisation to ensure that equation 3 is satisfied after each iteration. The fraction of particles outside the size range accessible to the range of frequencies used may also be inferred using the gamma-ray density measurement as will be discussed in more detail below.

The range of particle sizes accessible to this method can be calculated using various theoretical models such as those described by Harker, A. and Temple, J. in "Velocity and attenuation of ultrasound in suspensions of particles in fluids" J. Physics D: Applied Physics 21, 1576–88 and by McClements, D. J. and Povey, M. J. W., in "Ultrasonic Velocity as a Probe of Emulsions and Suspensions", Advances in Colloid and Interface Science 27, 285–316, the contents of both being incorporated herein by way of cross reference. The theoretical model of Harker and Temple (1988) has been used in this embodiment due to a combination of accuracy and ease of use.

FIG. 1 shows the calculated ultrasonic velocity as a function of frequency for suspensions of various particle sizes. To interpret the curves in FIG. 1 note that the velocity of ultrasound in slurries depends on the inertia of particles in the fluid under the influence of the ultrasonic wave. An ultrasonic wave passing through a fluid causes a periodic displacement of the fluid. At low frequencies very small particles tend to move in phase with the fluid so the velocity in the slurry of the ultrasound may differ considerably from the velocity in the pure suspending fluid. As particle size and ultrasonic frequency increases, the particles tend to lag more and more behind the movement of the fluid and the ultrasonic velocity approaches that of the suspension acting as a uniform fluid. There is a transition frequency range between complete entrainment and no entrainment of the particles. The centre frequency of this transition region shows a significant decrease with increasing particle diameter.

FIG. 1 shows that, for silica in water, ultrasonic velocity measurements in the frequency range 10 kHz to 50 MHz can be used to determine the particle size distribution of particles in the range of about 0.1 to 20 microns. It is the range in the frequency of ultrasound velocity measurements that restricts the range of the calculated particle size distribution. It is feasible to extend the technique to coarser particles by measuring at lower frequencies and to finer particles by using higher frequencies.

Figure 2:
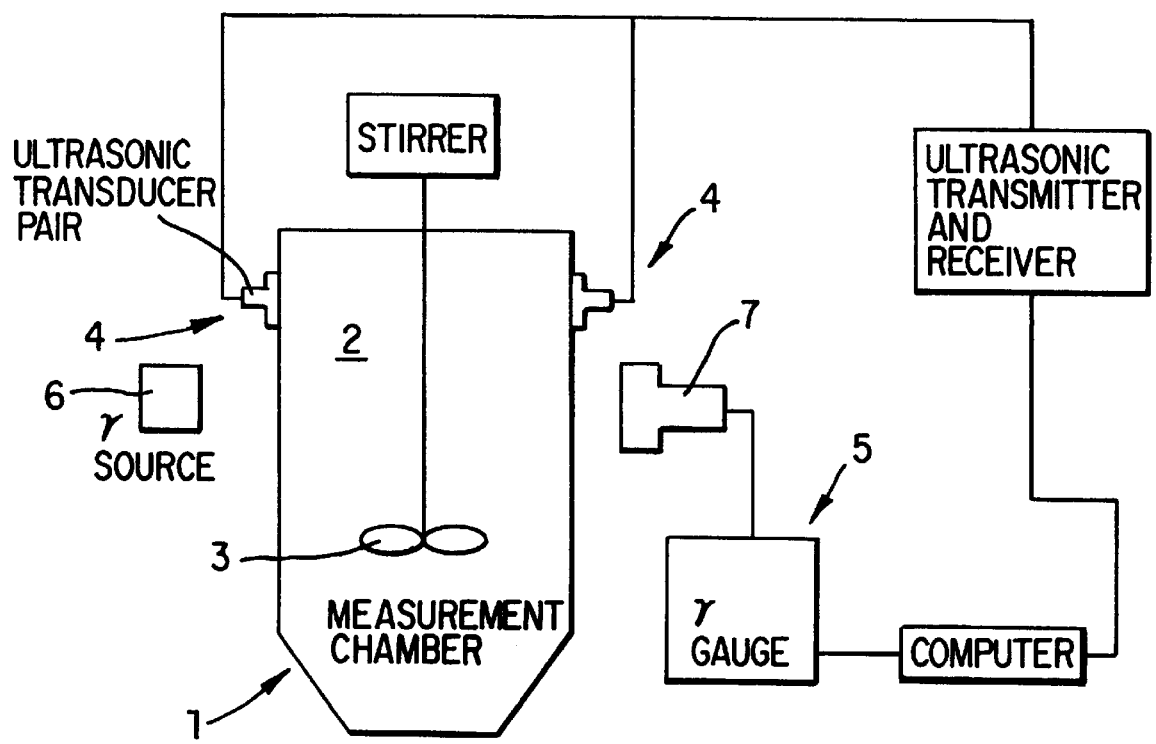
FIG. 2 is an apparatus according to the present invention as used during testing.

FIG. 2 shows a slurry measurement chamber 1 used in the testing of the invention. The chamber 1 contains the suspension 2 to be measured, which is a dispersion of unknown particle size and concentration. An agitator 3 (which may be a stirrer) is employed to keep the dispersion suspended and homogenous. An additional ultrasonic disperser may be used to keep the particles in suspension. In industrial applications, chamber 1 may be replaced by a pipe through which the slurry of interest is pumped.

This embodiment of the invention uses six pairs of piezoelectric transducers 4 to transmit and receive ultrasound of specific frequency. Alternatively, use can be made of lesser number of broadband ultrasonic transducers. Transducers 4 are aligned with the faces highly parallel and a Matec Instruments MBS 8000 was used to generate pulsing signals and to receive and amplify the transmitted signals. The transducers were excited in toneburst mode and the transit time of the pulse measured. Calibration was performed by measuring the transit time of ultrasonic pulses in water at different temperatures.

A gamma-ray attenuation density gauge 5 is used to measure the solids weight fraction of the slurry. A collimated 370 MBq (10 mCi) $^{137}$Cs gamma-ray source 6 is used and gamma-ray transmission detected with a 51×51 mm NaI(T1) detector and photomultiplier 7. The density may be derived from the gamma-ray transmission, as is known.

The experimental data is then inverted to give a particle size distribution. In some circumstances other inversion methods such as a correlation technique or a fill non-linear inversion procedure are preferable.

To further illustrate the method according to the invention a specific example of silica suspensions in water is given. More particularly, two standard suspensions of spherical silica particles of known particle size were measured, one with a mean diameter of 1.0 microns and the other with a mean diameter of 1.5 microns. The size distribution of these samples was supplied by the manufacturer and confirmed by measurements on a laser diffraction particle size analyser. The theoretical model of Harker and Temple (1988) was used to provide a velocity spectrum. For volume fractions less than 15% by volume the model is approximately linear and so no perturbation scheme was necessary.

Figure 3:
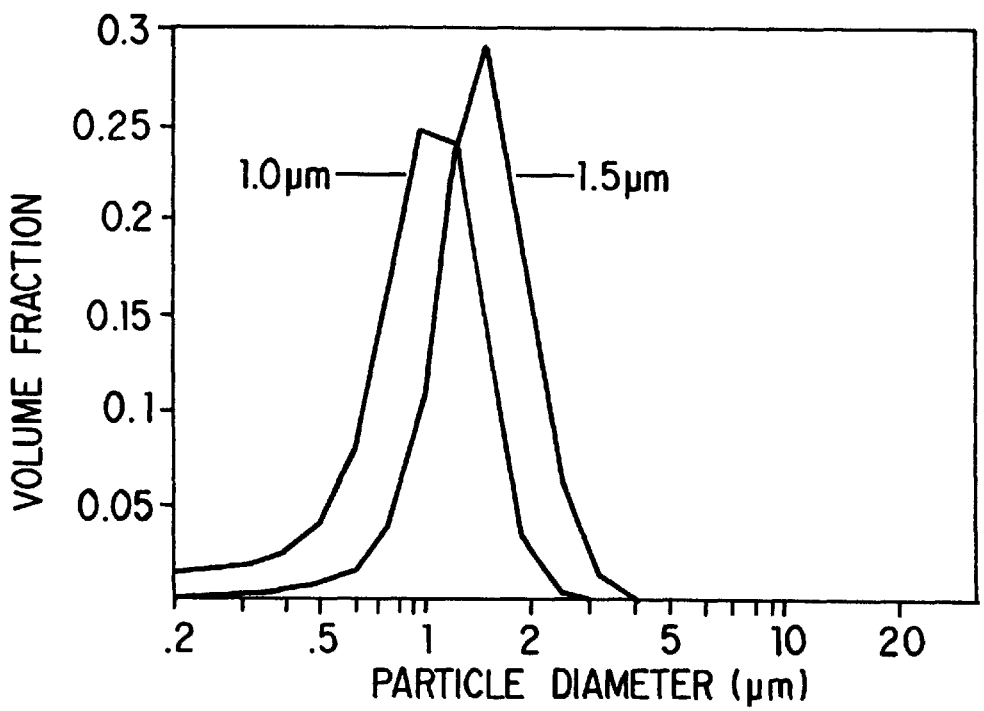
FIG. 3 is the results of the inversion procedure for 1.0 $\mu$m and 1.5 $\mu$m diameter test silica suspensions using the apparatus and method according to the invention.

The results of the inversion procedure for the 1.0 micron and 1.5 micron diameter silica suspensions are shown in FIG. 3. The method shows good discrimination between the two suspensions. The volume density for both solutions was measured to be approximately 10%. For the nominal 1.0 micron sample the mean particle size was measured to be 0.94 micron whereas for the 1.5 micron distribution it was measured as 1.43 micron. These results represent good agreement between the present method and laser diffraction. The measured width of the size distributions shown in FIG. 3 is relatively large because of the experimental errors in velocity determination and because of the small number of frequencies used.

Figure 4:
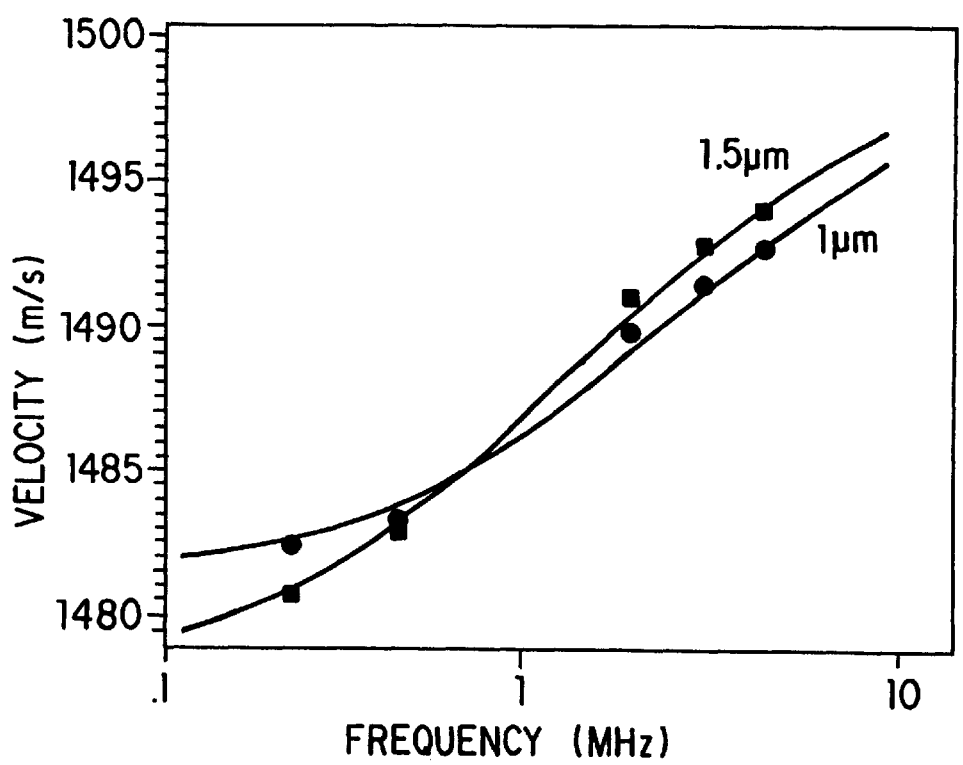
FIG. 4 illustrates the measured velocity spectrum giving rise to the results in FIG. 3.
Figure 5:
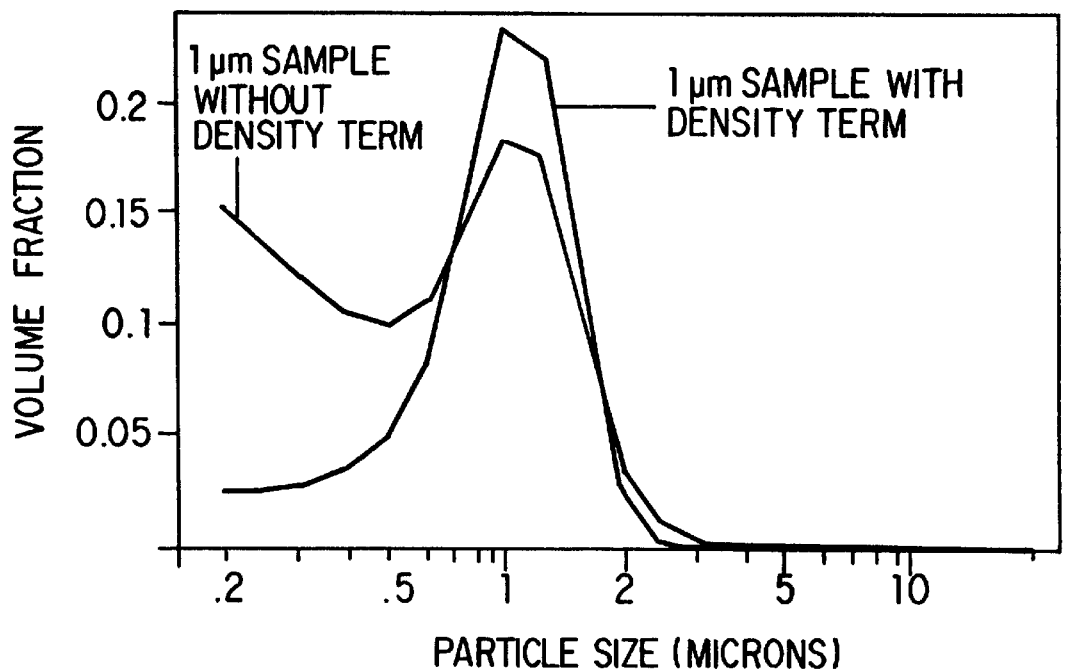
FIG. 5 illustrates the results for the 1.0 $\mu$m diameter test silica sample with and without a density correction.

The experimental data for the two suspensions is graphed in FIG. 4 (dots for the 1.0 micron sample and squares for the 1.5 micron sample) along with the velocities calculated for the particle size distributions of FIG. 3 (unbroken lines). The inversion method has produced an accurate result for the particle size despite errors irr the individual measurements shown in FIG. 4. This favourable result is achieved in part due to the use of the density gauge which places a tight constraint on the inversion. Without use of the density measurement the invention can still provide useful results in some cases, as could be determined by those skilled in the art. FIG. 5 shows the inversion for the 1.0 micron silica sample with and without the constraint in place. Spurious high concentrations of fine particle size (less than 0.5 microns) are generated in the unconstrained case while the RMS error of the fit to the ultrasonic velocity data is improved. This illustrates the importance of the density constraint in improving the resolution of the inversion technique. The choice of inversion method is also important in producing a good inversion as it limits the degree of oscillation present in the solution.

Figure 6:
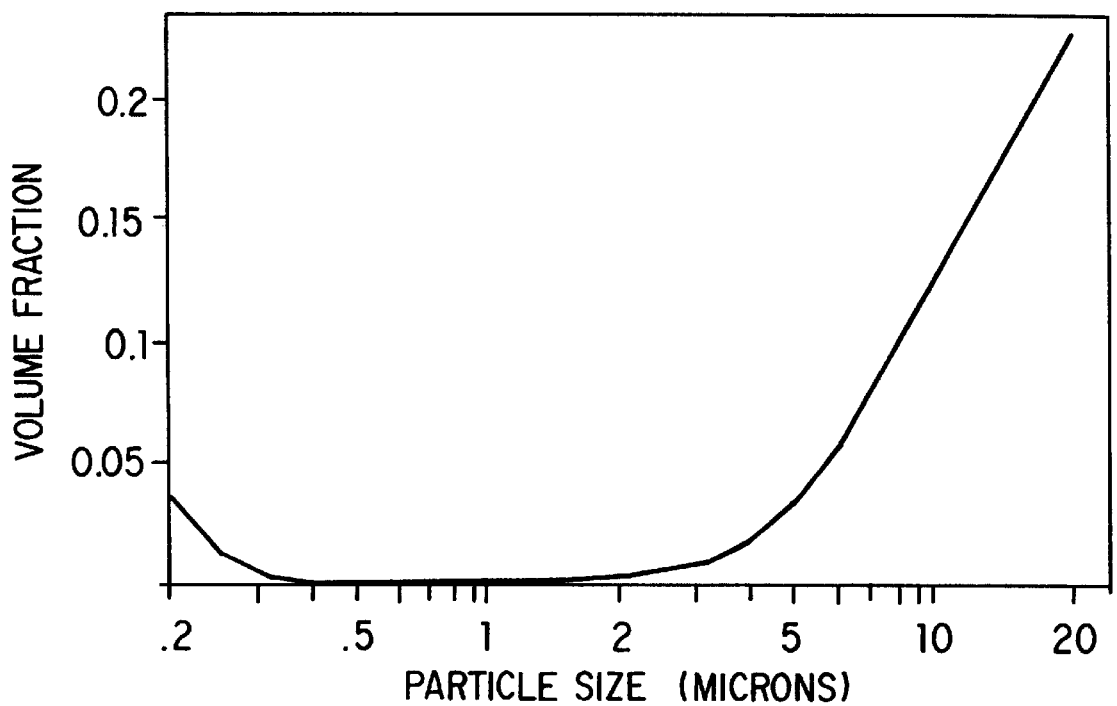
FIG. 6 illustrates the particle size distribution for an oversize coarse SiC sample.

In the above example, the particle size of the silica corresponds to the central part of the frequency range covered by the measurements. In order to evaluate the method on a sample containing out of range particles, a coarse SiC sample with a mean diameter of approximately 20 microns was used. Measurements were again made at the same frequencies as for the silica. FIG. 6 shows the results of inverting that data. The program correctly assigns almost all the material to the coarse end of the particle size spectrum.

One application of the ultrasonic velocity technique is in the improved control of dispersion in the paint and pigment industry. Dispersion is aimed at breaking down agglomerations of the 0.2 micron diameter $TiO_2$ particles. After dispersion the majority of particles are agglomerations of a few basic units. Two $TiO_2$ dispersions were provided by industry, one well and the other poorly dispersed. Measurement of these dispersions also provides a test of the invention in conditions where the particle size distribution is polydisperse unlike those in the test cases described above.

Figure 7:
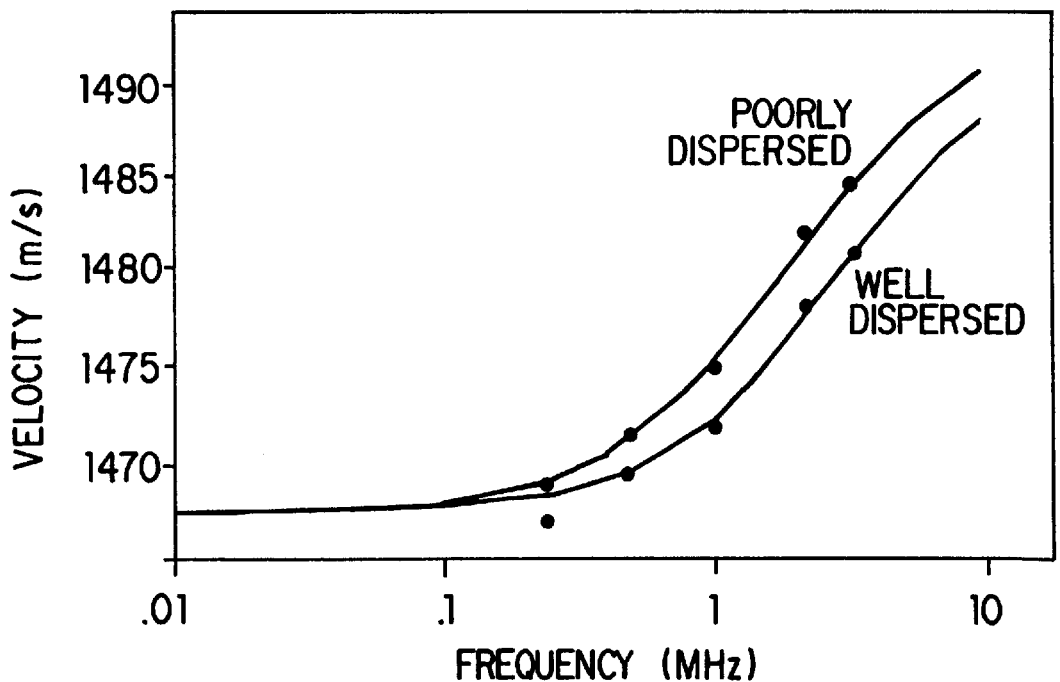
FIG. 7 shows the measured and theoretical values of velocity as a function of frequency for two $TiO_2$ suspensions.

In the present work, measurements were made on the two dispersions at a solid content of 2.3% by volume. FIG. 7 shows the measured and theoretical values of velocity as a function of frequency. The results show discrimination of the two samples. In the present case, high accuracy velocity measurements were made over the frequency range 0.25 to 3.5 MHz. Therefore, the present measurements are not very sensitive to particles of diameter less than about 0.3 microns or greater than about 10 microns.

Figure 8:
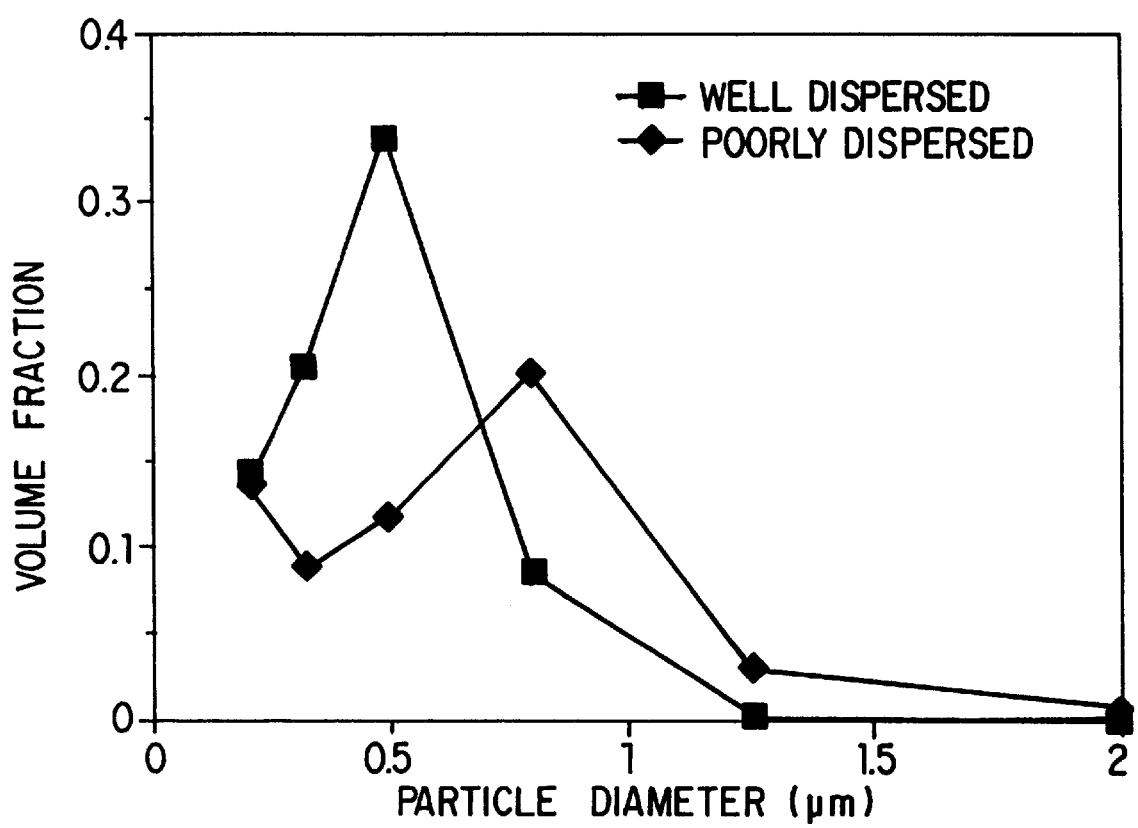
FIG. 8 illustrates the particle size distribution obtained by the invention for two $TiO_2$ suspensions.

Application of an inversion algorithm to the data shown in FIG. 7 yields the particle size distributions shown in FIG. 8. The d50 for particles finer than 2.0 microns is 0.38 microns for the well dispersed sample and 0.53 microns for the poorly dispersed sample. The fraction of particles greater than 2.0 microns estimated by the present method and is 0.33 for the poor sample and 0.16 for the good sample.

Measurements were made of both dispersions by optical diffraction techniques. The dispersions had to be diluted to 0.004% to allow sufficient optical transmission. Stirring was kept to a minimum in the measurement and no ultrasonic dispersion was used to avoid breaking up the agglomerates. The d50 measured by the optical method was 0.36 micron for the poor and 0.35 micron for the good dispersions. The optical and ultrasonic techniques display good agreement for the well dispersed sample not for the poorly dispersed sample. This can be explained, however, by the extreme dilution which causes the agglomerates in the poorly dispersed sample to a break up. In any event this illustrates the disadvantage of prior art methods such as optical diffraction techniques.

Alternatively, information about the particle size distribution can be presented in a simpler fashion. For the above $TiO_2$ example, a parameter R may be defined as $$R=(V_{1.0}-V_{0.5})/(V_{3.5}-V_{2.25}) \quad (5)$$

where $V_x$ is the ultrasonic velocity at x MHz. As particle size changes, the curve in FIG. 1 moves either to the left or right changing the ratio R quite strongly. This ratio is insensitive to temperature and concentration fluctuations and therefore may be used as a figure of merit for dispersion. The value of R was measured as 1.40±0.05 for the poor dispersion and 0.90±0.05 for the good dispersion. Such a single parameter provides a simple criteria for the adequacy of the dispersion process.

Although the invention has been described with reference to a particular example, it will be appreciated by those skilled in the art that it may be embodied in many other forms.

We claim:

1. A method for determining the size distribution of particles in a fluid, the method including the steps of:

(a) passing a plurality of ultrasonic beams through the fluid, wherein the beams have respective frequencies $f_1$, $f_2$, . . . $f_n$;

(b) obtaining a velocity measure of the beams in the fluid;

(c) obtaining an ultrasonic velocity spectrum as a function of particle size for the fluid; and (d) calculating the particle size distribution for the particles in the fluid from the velocity measure and the velocity spectrum which were respectively obtained in steps (b) and (c).

2. A method according to claim 1 wherein the ultrasonic velocity spectrum is obtained either by prior experiment or calculation.

3. A method according to claim 2 wherein step (b) includes determining the difference in velocity of the beams having frequencies $f_i$ and $f_{i+1}$.

4. A method according to claim 1 wherein step (c) includes transforming the velocity spectrum into a linear form.

5. A method according to claim 4 wherein step (b) includes determining the difference in velocity of the beams having frequencies $f_i$ and $f_{i+1}$.

6. A method according to claim 4 wherein step (d) includes an inversion of the linear form.

7. A method according to claim 6 wherein step (b) includes determining the difference in velocity of the beams having frequencies $f_i$ and $f_{i+1}$.

8. A method according to claim 1 further including the steps of:

(e) passing gamma rays through the fluid;

(f) determining from the attenuation of the gamma-rays the density of the fluid; and (g) calculating the particle size distribution of the particles in the fluid from the velocity measure, the velocity spectrum, and the density measure respectively obtained during steps (b), (c) and (f).

9. A method according to claim 8 wherein step (b) includes determining the difference in velocity of the beams having frequencies $f_i$ and $f_{i+1}$.

10. A method according to claim 8 wherein step (g) includes an inversion of the linear form to give the particle size distribution in a certain size range.

11. A method according to claim 10 wherein the amount of particles outside the inversion size range is also calculated.

12. A method according to claim 11 wherein step (b) includes determining the difference in velocity of the beams having frequencies $f_i$ and $f_{i+1}$.

13. A method according to claim 10 wherein step (b) includes determining the difference in velocity of the beams having frequencies $f_i$ and $f_{i+1}$.

14. A method according to any claim 1 wherein step (b) includes determining the difference in velocity of the beams having frequencies $f_i$ and $f_{i+1}$.

15. A method according to claim 1 wherein step (b) includes determining the velocity of each of the beams.

16. An apparatus for determining the size distribution of particles in a fluid, the apparatus including:

a transducer for passing a plurality of ultrasonic beams through the fluid, wherein the beams have respective frequencies $f_1, f_2 \ldots f_n$;

a first processor for obtaining a velocity measure of said beams in the fluid;

second processor means for obtaining the ultrasonic velocity spectrum as a function of particle size for the fluid; and third processor means responsive to the a first and second processor for calculating the particle size distribution for the fluid.

17. An apparatus according to claim 16 wherein the first, second and third processors are incorporated in a single processor.

* * * * *

UNITED STATES PATENT AND TRADEMARK OFFICE
CERTIFICATE OF CORRECTION

PATENT NO. : 5,831,150
DATED : November 3, 1998
INVENTOR(S) : Brian David Sowerby, et. al.

It is certified that error appears in the above-identified patent and that said Letters Patent is hereby corrected as shown below:

| Column | Line | |
|---|---|---|
| 3 | 54 | Change "increases" to --increase--. |
| 4 | 51 | Change "micron" to --microns--. |
| 4 | 62 | Change "errors irr" to --errors in--. |
| 5 | 45 | After "method" delete "and". |
| 5 | 58 | Before "break" delete "a". |
| 6 | 6 | Change "criteria" to --criterion--. |
| 8 | 1 | Before "second" insert --a--; delete "means". |
| 8 | 5 | Before "third" insert --a--; delete "means"; before "first" delete "a". |

Signed and Sealed this

Twenty-first Day of September, 1999

Attest:

Q. TODD DICKINSON

*Attesting Officer*   *Acting Commissioner of Patents and Trademarks*